United States Patent
Mahlin

(10) Patent No.: US 10,470,713 B2
(45) Date of Patent: *Nov. 12, 2019

(54) SENSOR GUIDE WIRE DEVICE AND SYSTEM INCLUDING A SENSOR GUIDE WIRE DEVICE

(71) Applicant: ST. JUDE MEDICAL COORDINATION CENTER BVBA, Zaventum (BE)

(72) Inventor: Fredrik Mahlin, Uppsala (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 151 days.

This patent is subject to a terminal disclaimer.

(21) Appl. No.: 15/030,770

(22) PCT Filed: Oct. 23, 2014

(86) PCT No.: PCT/IB2014/002974
§ 371 (c)(1),
(2) Date: Apr. 20, 2016

(87) PCT Pub. No.: WO2015/059578
PCT Pub. Date: Apr. 30, 2015

(65) Prior Publication Data
US 2016/0262698 A1    Sep. 15, 2016

Related U.S. Application Data

(60) Provisional application No. 61/895,616, filed on Oct. 25, 2013.

(51) Int. Cl.
*A61M 25/09* (2006.01)
*A61B 5/00* (2006.01)
(Continued)

(52) U.S. Cl.
CPC .............. *A61B 5/6851* (2013.01); *A61B 5/01* (2013.01); *A61B 5/026* (2013.01); *A61B 5/0215* (2013.01);
(Continued)

(58) Field of Classification Search
CPC . A61B 5/6851; A61B 5/0215; A61B 5/02152; A61B 5/02158; A61B 5/026; A61M 2025/0002; A61M 2025/0003
See application file for complete search history.

(56) References Cited

U.S. PATENT DOCUMENTS 3,521,620 A    7/1970    Cook
4,456,013 A    6/1984    De Rossi et al.
(Continued)

FOREIGN PATENT DOCUMENTS

DE    24 20 610 A1    10/1975
EP    0 387 453 A1    9/1990
(Continued)

OTHER PUBLICATIONS

Japanese Office Action and English translation, dated Mar. 21, 2017, 14 pages.
(Continued)

*Primary Examiner* — David J. McCrosky
(74) *Attorney, Agent, or Firm* — Foley & Lardner LLP

(57) ABSTRACT

A sensor guide wire for an intravascular measurement of a physiological variable in a living body, may comprise a proximal tube portion; a distal end portion; and a sensor element configured to measure the physiological variable based on exposure to fluid in the living body. The sensor guide wire may further comprise a mounting structure supporting the sensor element in a freely suspended manner in a lumen within the sensor guide wire and/or a cylindrical-shaped jacket forming an interior space housing the sensor
(Continued)

element and extending from a distal end of the proximal tube portion to a proximal end of the distal end portion in which the outer circumferential wall of the jacket includes a plurality of slots located between at least one aperture of the outer circumferential wall and one of the distal and proximal ends of the jacket.

8 Claims, 9 Drawing Sheets

(51) Int. Cl.
  A61B 5/0215 (2006.01)
  A61B 5/01 (2006.01)
  A61B 5/026 (2006.01)
  A61B 5/145 (2006.01)
  A61M 25/00 (2006.01)

(52) U.S. Cl.
  CPC . *A61B 5/14503* (2013.01); *A61M 2025/0002* (2013.01); *A61M 2025/0003* (2013.01)

(56) References Cited

U.S. PATENT DOCUMENTS

| | | | |
|---|---|---|---|
| 4,712,566 | A | 12/1987 | Hok |
| 4,941,473 | A | 7/1990 | Tenerz et al. |
| 5,018,529 | A | 5/1991 | Tenerz et al. |
| 5,085,223 | A | 2/1992 | Lars et al. |
| 5,125,058 | A | 6/1992 | Tenerz et al. |
| 5,437,288 | A | 8/1995 | Schwartz et al. |
| 5,549,109 | A | 8/1996 | Samson et al. |
| RE35,648 | E | 11/1997 | Tenerz et al. |
| 5,993,378 | A | 11/1999 | Lemelson |
| 6,019,728 | A | 2/2000 | Iwata et al. |
| 6,045,734 | A | 4/2000 | Luther et al. |
| 6,162,182 | A | 12/2000 | Cole |
| 6,167,763 | B1 | 1/2001 | Tenerz et al. |
| 6,248,083 | B1 | 6/2001 | Smith et al. |
| 6,295,990 | B1 | 10/2001 | Lewis et al. |
| 6,343,514 | B1 | 2/2002 | Smith |
| 6,491,712 | B1 | 12/2002 | O'Connor |
| 7,011,636 | B2 | 3/2006 | Tenerz |
| 7,222,539 | B2 | 5/2007 | Tulkki |
| RE39,863 | E | 10/2007 | Smith |
| 7,724,148 | B2 | 5/2010 | Samuelsson et al. |
| 8,174,395 | B2 | 5/2012 | Samuelsson et al. |
| 8,461,997 | B2 | 6/2013 | Samuelsson et al. |
| 8,551,022 | B2 | 10/2013 | Von Malmborg |
| 9,144,664 | B2 | 9/2015 | Jacobsen et al. |
| 2002/0013540 | A1 | 1/2002 | Jacobsen et al. |
| 2002/0049392 | A1 | 4/2002 | Demello |
| 2002/0077520 | A1 | 6/2002 | Segal et al. |
| 2002/0173785 | A1 | 11/2002 | Spear et al. |
| 2003/0009208 | A1 | 1/2003 | Snyder et al. |
| 2003/0069522 | A1 | 4/2003 | Jacobsen et al. |
| 2005/0004515 | A1 | 1/2005 | Hart et al. |
| 2005/0043670 | A1 | 2/2005 | Rosenberg |
| 2005/0187487 | A1 | 8/2005 | Azizkhan et al. |
| 2005/0268725 | A1 | 12/2005 | Tulkki |
| 2006/0004346 | A1 | 1/2006 | Begg |
| 2006/0211946 | A1 | 9/2006 | Mauge et al. |
| 2007/0088220 | A1 | 4/2007 | Stahmann |
| 2008/0200770 | A1 | 8/2008 | Hubinette |
| 2009/0020961 | A1 | 1/2009 | Kameyama et al. |
| 2009/0062602 | A1 | 3/2009 | Rosenberg et al. |
| 2009/0177185 | A1 | 7/2009 | Northrop |
| 2010/0063479 | A1 | 3/2010 | Merdan et al. |
| 2010/0145308 | A1 | 6/2010 | Layman et al. |
| 2010/0152663 | A1 | 6/2010 | Darr |
| 2010/0217304 | A1 | 8/2010 | Angel et al. |
| 2010/0228112 | A1 | 9/2010 | Von Malmborg |
| 2010/0262041 | A1* | 10/2010 | Von Malmborg ... A61B 5/0215 600/585 |
| 2011/0004198 | A1 | 1/2011 | Hoch |
| 2011/0160648 | A1 | 6/2011 | Hoey |
| 2011/0160680 | A1 | 6/2011 | Cage et al. |
| 2011/0213220 | A1 | 9/2011 | Samuelsson et al. |
| 2011/0245808 | A1 | 10/2011 | Voeller et al. |
| 2012/0289808 | A1 | 11/2012 | Hubinette |
| 2013/0102927 | A1 | 4/2013 | Hilmersson |
| 2013/0102928 | A1 | 4/2013 | Sotos et al. |
| 2013/0274618 | A1 | 10/2013 | Hou et al. |
| 2013/0296718 | A1 | 11/2013 | Ranganathan et al. |
| 2014/0058338 | A1 | 2/2014 | Adams et al. |
| 2014/0180066 | A1 | 6/2014 | Stigall |
| 2015/0173629 | A1 | 6/2015 | Corl et al. |
| 2016/0249821 | A1 | 9/2016 | Boye et al. |

FOREIGN PATENT DOCUMENTS

| | | |
|---|---|---|
| EP | 0 521 595 B1 | 5/1999 |
| EP | 1 340 516 A1 | 9/2003 |
| EP | 0 877 574 B1 | 10/2003 |
| EP | 1 849 409 A1 | 10/2007 |
| EP | 2 085 108 A2 | 8/2009 |
| EP | 1 545 680-81 | 9/2010 |
| SE | 441725 B | 11/1985 |
| SE | 453561 B | 2/1988 |
| SE | 454045 B | 3/1988 |
| SE | 460396 B | 10/1989 |
| SE | 469454 B | 7/1993 |
| WO | WO-97/00641 A1 | 1/1997 |
| WO | WO-00/69323 A2 | 11/2000 |
| WO | WO-03/094693 A2 | 11/2003 |
| WO | WO-2004/011076 A2 | 2/2004 |
| WO | WO 2004/011076 A2 | 5/2004 |
| WO | WO-2007/050718 A1 | 5/2007 |
| WO | WO-2009/020954 A1 | 2/2009 |
| WO | WO-2009/029639 A1 | 3/2009 |
| WO | WO-2009/054803 A1 | 4/2009 |
| WO | WO-2009/0112060 A1 | 9/2009 |
| WO | WO-2011/041720 A2 | 4/2011 |
| WO | WO 2012000798 A1 * | 1/2012 ........... A61B 5/0215 |
| WO | WO-2016/138226 A1 | 9/2016 |

OTHER PUBLICATIONS

Japanese Office Action and English translation, Application No. 2016-525613, dated Dec. 5, 2017, 6 pages.
"In", The American Heritage Dictionary of the English Language, Fifth Edition (2014)Houghton Mifflin Harcourt Publishing Company, pp. 1-3, Retrieved from <https://ahdictionary.co/word/search.html?q-IN> on Mar. 25, 2015.
"-Like". 2011. In the American Heritage Dictionary of the English Language, Boston: Houghton Mifflin. <http://search.credoreference.com/content/entry/hmdictenglang/like/0>.
European Office Action, Application No. 13 723 953.9, dated Jun. 27, 2017, 6 pages.
International Preliminary Report on Patentability, PCT/IB2013/000903, dated Nov. 13, 2014, 11 pages.
International Search Report and Written Opinion, PCT/US2016/019498, dated Jul. 4, 2016, 17 pages.
International Preliminary Report on Patentability, PCT/US2016/019498, dated Sep. 8, 2017, 11 pages.
Machine translation of DE 2420610.
PCT/ISA/206, International Application No. PCT/US2016/019498, 7 pages.
Radi Medical Systems AB, PressureWire Certus, Brochure, 60680 Rev. 03, Apr. 2008.
tube.Dictionary.com, Dictionary.com Unabridged, Random House, Inc., http://dictionary.reference.com/browse/tube> (accessed: Sep. 5, 2014).
USPTO Notice of Allowance, U.S. Appl. No. 13/804,342, dated Sep. 5, 2017, 7 pages.
USPTO Notice of Allowance, U.S. Appl. No. 13/804,342, dated May 10, 2018, 8 pages.
USPTO Office Action, U.S. Appl. No. 13/804,342, dated Jan. 16, 2015, 9 pages.

(56) References Cited

OTHER PUBLICATIONS

USPTO Office Action, U.S. Appl. No. 13/804,342, dated Nov. 19, 2015, 12 pages.
USPTO Office Action, U.S. Appl. No. 13/804,342, dated Sep. 12, 2014, 18 pages.
USPTO Office Action, U.S. Appl. No. 13/804,342, dated Apr. 7, 2016, 13 pages.
USPTO Office Action, U.S. Appl. No. 13/806,380, dated Sep. 24, 2014, 19 pages.
USPTO Office Action, U.S. Appl. No. 13/806,380, dated Apr. 1, 2015, 18 pages.
USPTO Office Action, U.S. Appl. No. 13/806,380, dated Aug. 4, 2017, 15 pages.
USPTO Office Action, U.S. Appl. No. 13/806,380, dated Jan. 30, 2018, 18 pages.
USPTO Office Action, U.S. Appl. No. 13/806,380, dated Feb. 1, 2016, 18 pages.
European Office Action, dated Jul. 20, 2018, 6 pages.
USPTO Office Action, U.S. Appl. No. 13/806,380, dated Oct. 31, 2018, 14 pages.
USPTO Notice of Allowance, U.S. Appl. No. 13/804,342, dated Oct. 18, 2018, 14 pages.
European Extended Search Report, dated Nov. 19, 2018, 6 pages.
U.S. Appl. No. 16/366,112, filed Mar. 27, 2019, Ness, Peter J.
ASM Int'l, Materials and Coatings for Medical Devices: Cardiovascular. 2009. p. 417-419.
Harris et al, New Polyethylene Glycols for Biomedical Applications, Water-Soluble Polymers. ACS Symposium Series; American Chemical Society. 1991. p. 418-429.
USPTO Notice of Allowance, U.S. Appl. No. 13/806,380, dated May 22, 2019, 7 pages.
USPTO Office Action, U.S. Appl. No. 15/053,308, dated Apr. 4, 2019, 13 pages.
USPTO Office Action, U.S. Appl. No. 15/053,308, dated May 23, 2018, 13 pages.
USPTO Office Action, U.S. Appl. No. 15/053,308, dated Nov. 6, 2017, 14 pages.
Zalipsky et al, Introduction to Chemistry and Biological Applications of Poly(ethylene glycol). ACS Symposium Series; American Chemical Society. 1997. p. 1-13.
International Search Report and Written Opinion, PCT/US2019/024292, dated Jun. 26, 2019, 11 pages.

\* cited by examiner

SENSOR GUIDE WIRE DEVICE AND SYSTEM INCLUDING A SENSOR GUIDE WIRE DEVICE

FIELD OF THE INVENTION

The invention generally relates to the area of medical devices. More particularly, the present invention concerns a sensor guide wire device for intravascular measurements of a physiological variable, e. g. pressure or temperature, inside a living human or animal body, and also to a system for intravascular measurements of a physiological variable in a living body.

BACKGROUND

In many medical procedures, medical personnel wish to monitor various physiological conditions that are present within a body cavity of a patient. These physiological conditions are typically physical in nature, such as, for example, pressure and temperature, and provide the physician or medical technician with information as to the status of a patient's condition. The manner by which these types of parameters are measured and monitored should be as safe, as accurate and as reliable as possible.

Equipment and processes have been developed for assisting medical personnel, such as physicians or medical technicians, in diagnosing physiological conditions of a patient. For example, sensor guide wires in which a sensor is mounted at the distal end thereof have been developed. The sensor may, for example, be an intra-vascular pressure sensor that is arranged to measure blood pressure at various points within the vasculature to facilitate locating and determining the severity of, for example, stenosis or other disruptors of blood flow within the vessels of the living body.

SUMMARY

According to one embodiment of the present invention, a sensor guide wire for an intravascular measurement of a physiological variable in a living body, may comprise: a proximal tube portion; a distal end portion; a sensor element configured to measure the physiological variable based on exposure to fluid in the living body; and a cylindrical-shaped jacket forming an interior space housing the sensor element and extending from a distal end of the proximal tube portion to a proximal end of the distal end portion. The jacket comprises an outer circumferential wall with a circumferential surface extending between distal and proximal longitudinal ends of the jacket. The outer circumferential wall includes at least one aperture along its circumferential surface so as to permit passage of the fluid through the outer circumferential wall. The outer circumferential wall further includes a plurality of slots located between the at least one aperture of the outer circumferential wall and one of the distal and proximal ends of the jacket.

According to another embodiment of the present invention, a sensor guide wire for an intravascular measurement of a physiological variable in a living body, may comprise: a proximal tube portion; a distal end portion; a sensor element configured to measure the physiological variable based on exposure to fluid in the living body; and a mounting structure supporting the sensor element in a freely suspended manner in a lumen within the sensor guide wire.

According to another embodiment of the present invention, a sensor guide wire for an intravascular measurement of a physiological variable in a living body, may comprise a proximal tube portion; a distal end portion; and a sensor element configured to measure the physiological variable based on exposure to fluid in the living body. The sensor guide wire may further comprise a mounting structure supporting the sensor element in a freely suspended manner in a lumen within the sensor guide wire and/or a cylindrical-shaped jacket forming an interior space housing the sensor element and extending from a distal end of the proximal tube portion to a proximal end of the distal end portion in which the outer circumferential wall of the jacket includes a plurality of slots located between at least one aperture of the outer circumferential wall and one of the distal and proximal ends of the jacket.

It is to be understood that both the foregoing general description and the following detailed descriptions are exemplary and explanatory only, and are not restrictive of the invention as claimed.

BRIEF DESCRIPTION OF THE DRAWINGS

The features, aspects and advantages of the present invention will become apparent from the following description, appended claims, and the accompanying exemplary embodiments shown in the drawings, which are briefly described below.

DETAILED DESCRIPTION

Figure 1:
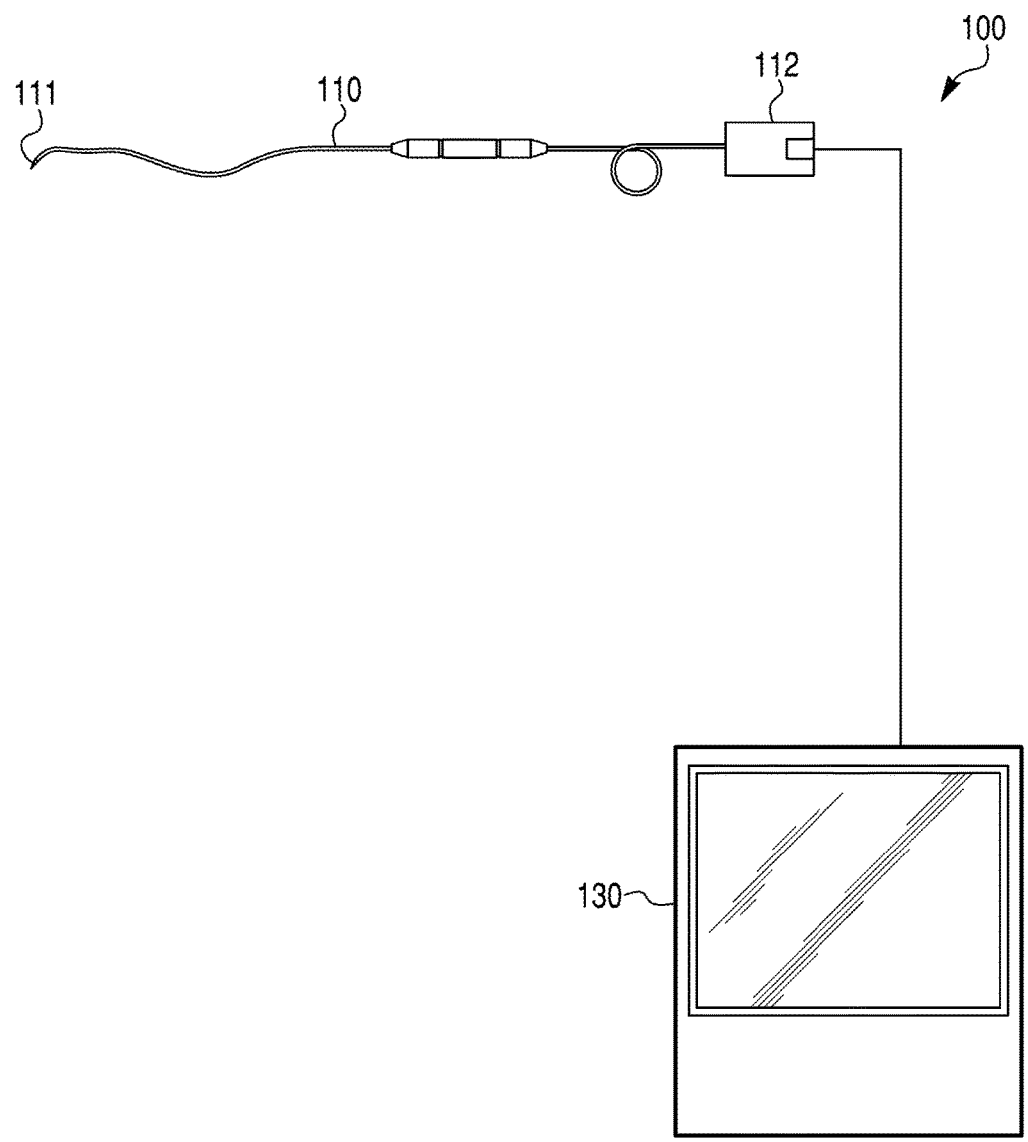
FIG. 1 is a schematic drawing showing a system for intravascular measurement according to one embodiment of the present invention.

FIG. 1 shows a system 100 comprising a sensor guide wire assembly according to one embodiment of the present invention. The arrangement comprises a sensor guide wire assembly 110, and a physiological monitor 130. The sensor guide wire assembly 110 may comprise a sensor element 111 arranged at the distal end of the sensor guide wire assembly 110. The sensor element 111 may be arranged to sense a physiological variable in a living body, such as a human or animal body, and provide a sensor signal. The sensor guide wire assembly 110 is a disposable device which typically includes a proximal connector 112 (which may be a female or male connector) for connection to the physiological monitor 130 which processes the sensor signal to generate a measurement of the physiological variable. Alternatively, a signal converting device or an interfacing device may be disposed between the proximal connector 112 and the physiological monitor 130, such as for example, the signal converting and interfacing devices disclosed in U.S. Patent Application Publication No. 2012/0289808, which is hereby incorporated by reference in its entirety for their teachings related to signal converting and interfacing devices, the use of physiological monitors, and the structure and use of sensor guide wire devices. Such a signal converting or interfacing device may be arranged to interface the sensor element 111 to the physiology monitor 130 such that a signal indicative of the physiological variable sensed by the sensor element 111 is pre-processed and forwarded to the physiology monitor 130. According to other embodiments, the sensor guide wire assembly 110 can communicate via wireless transmission with the physiological monitor 130 such as, for example, the wireless transmission arrangement disclosed in U.S. Pat. Nos. 7,724,148; 8,174,395; and 8,461,997, which are hereby incorporated by reference in their entireties for their teachings related to wireless transmission arrangements between sensor guide wires and physiological monitors, and the structure and use of sensor guide wire devices.

Figure 2:
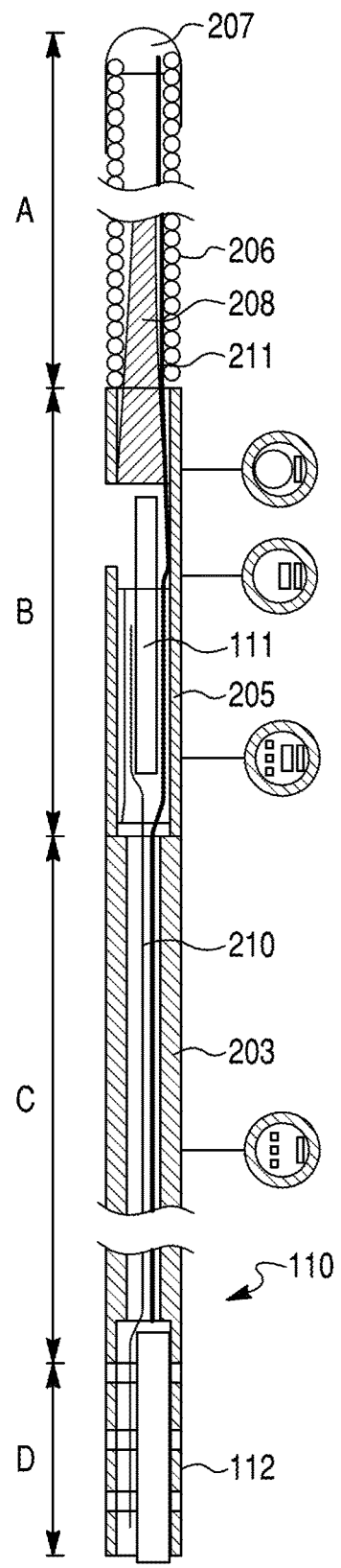
FIG. 2 is a cross-sectional view of a sensor guide wire used in the system of FIG. 1 according to one embodiment of the present invention.

FIG. 2 shows a sensor guide wire 110 that can be used in the system of FIG. 1. The sensor guide wire assembly 110 comprises the proximal connector 112, a flexible proximal tube portion 203, a jacket or sleeve 205, a distal end portion having a coil 206 and a tip 207, a distal core wire 208, and the sensor element 111, which is connected to the connector 112 by at least one electrical lead or microcable or optical signal line 210. In use, the connector 112 at the proximal end of the proximal tube portion 203 is inserted into a corresponding connector, such that measurement signals from the sensor element 111 can be displayed, for example as curves or numbers, on a suitable display on the physiology monitor 130. The sensor guide wire assembly 110 may optionally comprise a safety wire 211, which is attached in the tip 207 and extends preferably to the proximal connector 112. In case of an accidental break of the sensor guide wire assembly 110 when, for example, a doctor tries to push the sensor guide wire assembly 110 through a sharp bend in an artery of a patient, the safety wire 211 will make it possible to retrieve all parts of the sensor guide wire assembly 110 from the patient's artery. The safety wire 211 may also be helpful during manufacturing of the sensor guide wire assembly 110 in that the safety wire 211 can act as a guide when the different parts are assembled and threaded over each other. The safety wire 211 may alternatively have a shorter extension along the sensor guide wire assembly 110, typically from the tip 207 to the jacket 205.

In FIG. 2, the capital letters A to D represent the length of the different sections of the sensor guide wire assembly 110, and the following intervals should represent exemplifying lengths of the respective sections:

A=the length of the distal end portion=about 2 cm to about 3 cm;
B=the length of the jacket or sleeve 205=about 0.5 mm to about 10 mm, preferably about 1 mm to about 3 mm;
C=the length of the proximal tube portion 203=about 135 cm to about 340 cm, preferably about 160 cm to about 300 cm:
D=the length of the proximal connector 112=about 500 mm to about 1500 mm, preferably about 1040 mm.

The diameter of the sensor guide wire assembly 110 preferably varies between about 0.25 to about 2.5 mm; for use in coronary arteries, for example, the diameter is normally about 0.35 mm. In the context of length, width, diametrical, and other spatial dimensions, the modifier "about" can include a deviation of plus or minus 0 to 10% of the amount it modifies, preferably plus or minus 0 to 5% of the amount it modifies.

It should in particular be noted that the length of the jacket or sleeve 205 is rather small in comparison with the total length of the sensor guide wire assembly. For example, the jacket or sleeve 205 can range about 0.01% to 5% of the total length of the sensor guide wire assembly, preferably 0.025% to 2.5% of the total length of the sensor guide wire assembly, more preferably 0.05% to 1.5% of the total length of the sensor guide wire assembly.

It can further be seen that the flexible tube portion 203 may constitute the major portion of the length of the sensor guide wire assembly. Such a flexible tube portion can be made from stainless steel and is, for example, described in the U.S. Pat. Re. 35,648, herein incorporated by reference in its entirety for its teachings related to flexible tubes for sensor guide wire assemblies, and the structure and use of sensor guide wire devices. It should, however, be noted that-in contrast to the disclosure of Re 35,648, there is no core wire present in the proximal tube portion 203 of the sensor guide wire assembly in this embodiment of the present invention. This means that the walls of the flexible tube portion 203 may be made thicker without adversely limiting the space available for the sensitive electrical lead(s) extending from the sensor element 111 to the proximal connector 112. The core wire 208 then only extends in the distal end portion of the sensor guide wire assembly 110.

Figure 3:
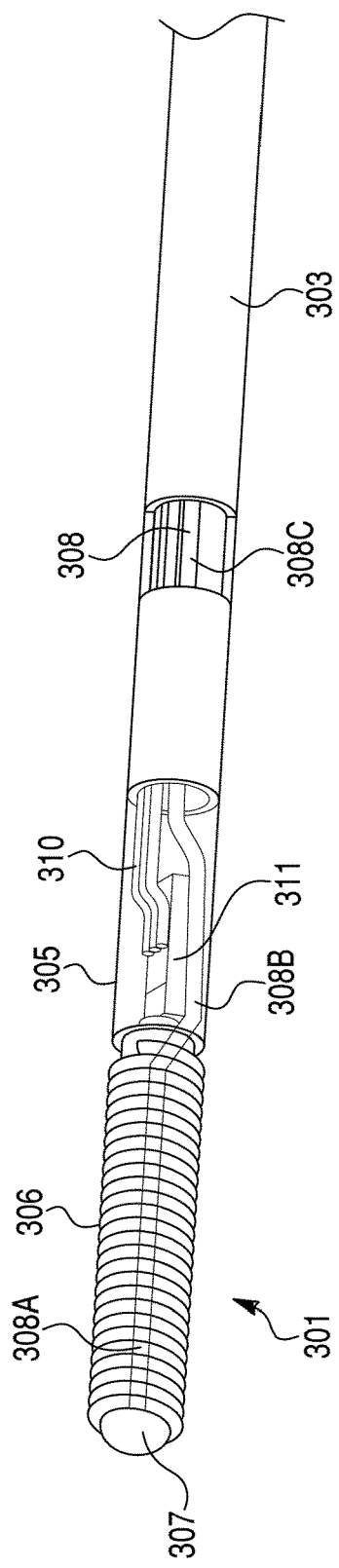
FIG. 3 is a cut away view of a sensor guide wire used in the system of FIG. 1 according to one embodiment of the present invention.

The sensor guide wire assembly 301 of FIG. 3 is another example of a sensor guide wire assembly that can be used in the system of FIG. 1. The sensor guide wire assembly 301 includes the sensor element 311; a distal end portion having a distal tip 307 and a coil 306, a core wire 308, a jacket or sleeve 305 (whose outline is only shown), one or more microcables or optical signal lines 310, and a proximal tube portion 303. The length and diameter dimensions mentioned in the context of the embodiment of FIG. 2 are also applicable for this embodiment. As with the embodiment of FIG. 2, the distal tip 307 is the most distal portion, i.e. that portion which is going to be inserted farthest into the vessel, and the proximal tube portion 303 is the most proximal portion, that is, that portion being situated closest to the connector 112 shown in FIG. 1.

The core wire 308 is shown in FIG. 3, and may comprise a first body portion 308A at the distal end portion, a sensor mounting portion 308B at the jacket or sleeve, and a second body portion 308C in the proximal tube portion (which is partially removed in the figure for sake of illustration). The sensor mounting portion 308B may or may not be an enlarged portion of the core wire 308 relative to the first body portion 308A and/or to the second body portion 308C in which the sensor element 311 is placed. However, the core wires 208 and 308 may have other configurations for mounting the sensor elements 111, 311 thereon. The core wire 308 and the core wire 208 may comprise any suitable material, such as for example, stainless steel or Nitinol (NiTi).

The sensor elements 111 and 311 may be used to sense any suitable physiological variable, such as, for example, pressure or temperature or flow. The sensor may be a microchip, a pressure sensitive device in the form of a membrane, a thermistor, a sensor for measuring the concentration or presence of a blood analyte, or other suitable pressure, temperature, or other variable-measuring device. Furthermore, the sensor element 111, 311 may be a plurality of sensor detecting devices. The physiological monitor 130 may use the sensor readings from the sensor element 111, 311 to determine blood pressure, blood temperature, blood flow, the concentration or presence of one or more blood analytes, and/or Fractional Flow Reserve measurements (FFR). In short, FFR is used to identify constrictions of coronary vessels, for example, in the great cardiac vein, by obtaining the ratio between the pressure distally and proximally of a constriction.

The sensor elements 111 and 311 are connected to the microcables or optical signal lines 210, 310 for transmitting signals between the sensor element 111, 311 in the distal part of the sensor guide wire 110, 301 and the connector 112 at the proximal end of the proximal tube portion 203, 303. Examples of suitable microcables are described, for example, in U.S. Patent Application Publication No. 2010/0228112, U.S. Patent Application Publication No. 2011/0213220, and U.S. Patent Application Publication No. 2012/0289808, all of which are hereby incorporated by reference in their entireties for their teachings related to microcables in guide wire assemblies and the structure and use of guide wire assemblies.

The distal tips 207 and 307 may comprise an arced tip, which is connected to their respective core wires 208, 308.

The coils 206 and 306 may be a radioopaque coil made of, for example, platinum, but any suitable material (radioopaque or not) may be used. The coil 206, 306 may be attached to the inner or outer circumference of the jacket 205, 305, or the outer circumference of an enlarged portion of the core wire 208, 308.

The proximal tube portions 203 and 303 may be made from any suitable material such as stainless steel or a super elastic alloy, such as Nitinol, copper-tin, copper-zinc, or copper-zinc-tin. The connector 112 is connected on the proximal end of the proximal tube portion 203, 303. According to one embodiment, the proximal section 203, 303 may be a hypo tube.

Figure 4:
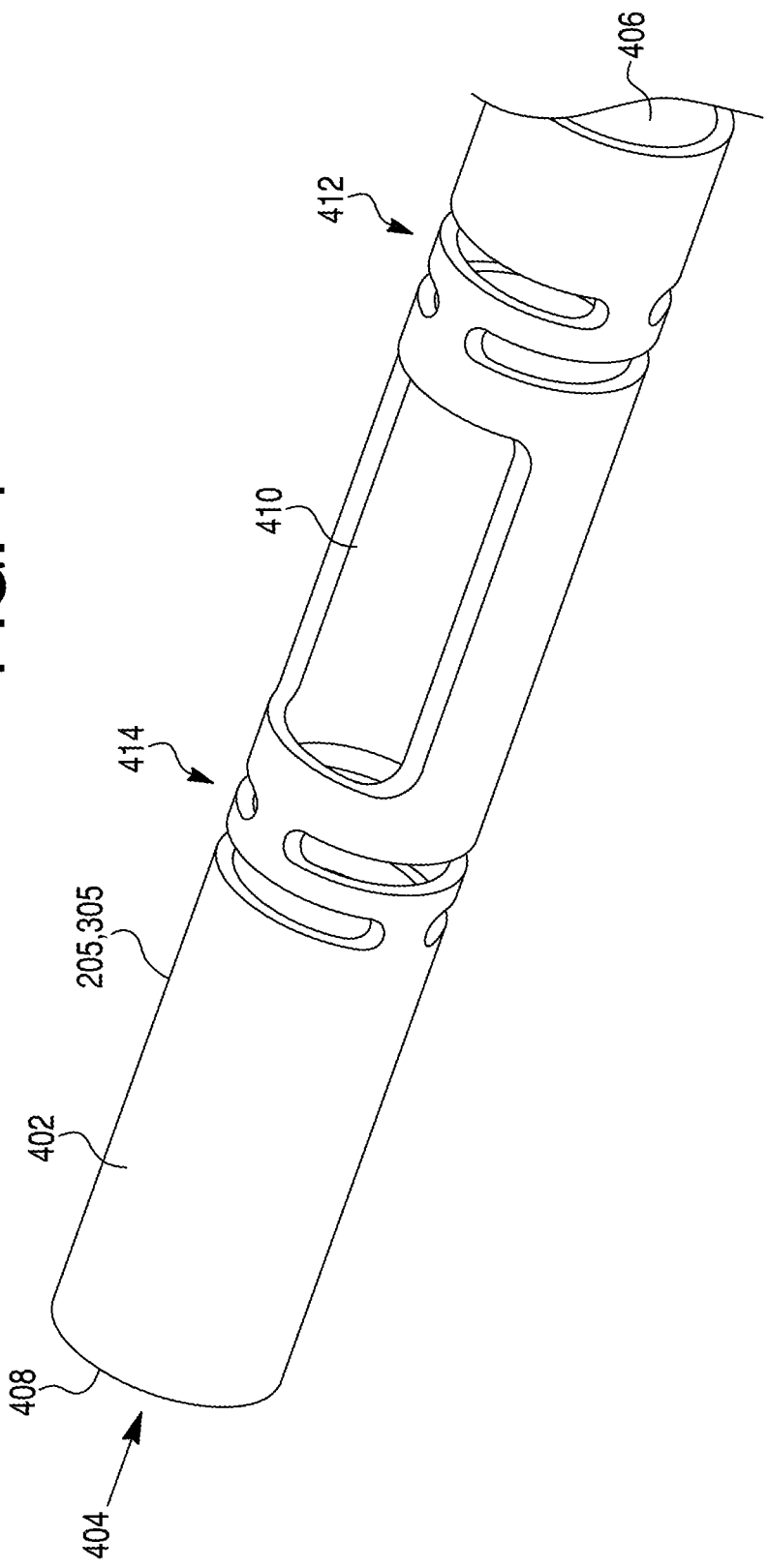
FIG. 4 shows a jacket according to one embodiment of the present invention.
Figure 5:
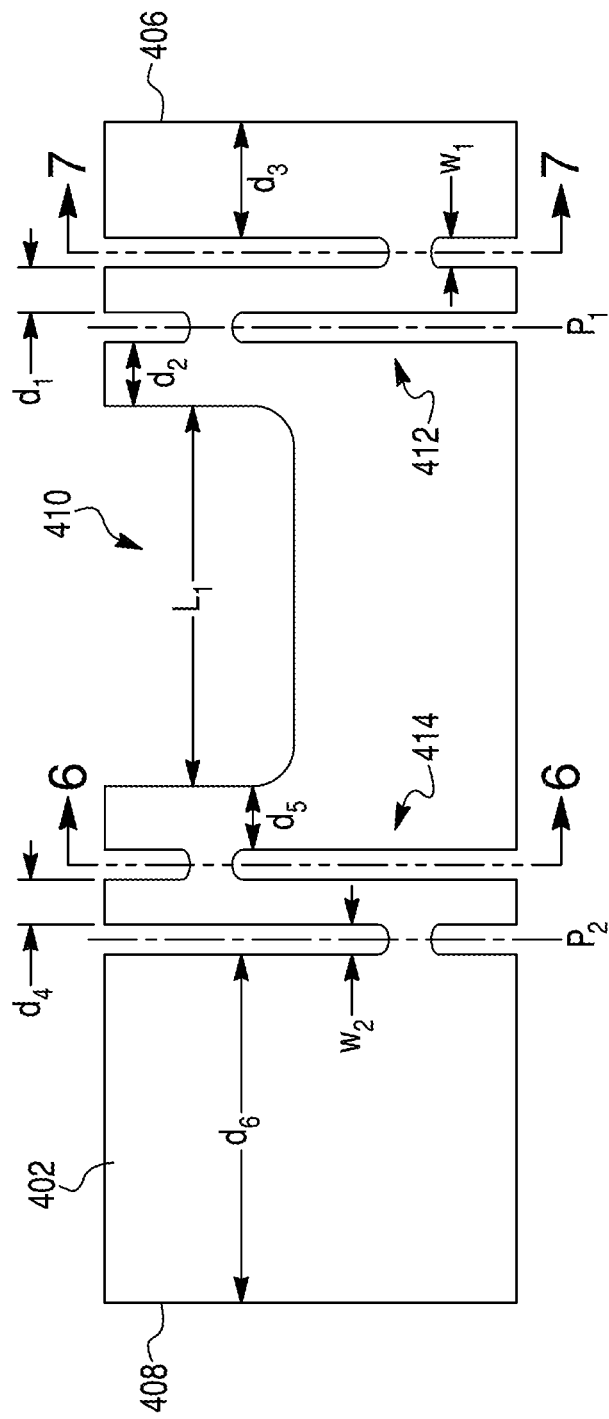
FIG. 5 shows a side view of the jacket of FIG. 4

The jacket 205, 305 that houses the sensor element 111, 311 is shown in FIGS. 4 and 5. The jacket 205, 305 is cylindrical and has an outer circumferential wall 402 through which a passageway 404 runs from a distal longitudinal end 406 to a proximal longitudinal end 408. The outer circumferential wall 402 comprises at least one aperture 410 along its circumferential surface so as to permit fluid passage through the outer circumferential wall 402 to the sensor element 311. The length $L_1$ of the aperture 410 may be any suitable length, such as for example between about 0.25 to about 2 mm, preferably about 0.7 mm. Furthermore, there may be two, three, four, or more apertures 410 which can be displaced along the longitudinal axis of the jacket or along the circumferential surface of the jacket or a combination thereof.

The outer circumferential wall 402 may include a plurality of slots 412 located between the at least one aperture 410 of the outer circumferential wall and the distal longitudinal end 406 or a plurality of slots 414 located between the at least one aperture 410 and the proximal longitudinal end 408 or both the pluralities of slots 412 and 414.

The plurality of slots 412 shown in FIGS. 4 and 5 comprises two slots in different perpendicular planes $P_1$ that runs perpendicular to a longitudinal axis such that main extensions of the slot is in their respective plane $P_1$. Each slot in the plurality of slots 412 may have a width $W_1$ and a length along its main extension. Preferably, the width $W_1$ of the slots 412 may be between about 0.01 to about 2.0 mm, preferably about 0.04 mm. As illustrated in FIG. 4, the slot in one perpendicular plane $P_1$ may be displaced in relation to the slot in an adjacent perpendicular plane $P_1$. Preferably, the slot in one perpendicular plane $P_1$ is displaced about 60° with respect to the slot in the adjacent perpendicular plane $P_1$. However, the degree of displacement may be any angle between 0° and 350°, such as any integer between 0° and 350°.

Figure 7:
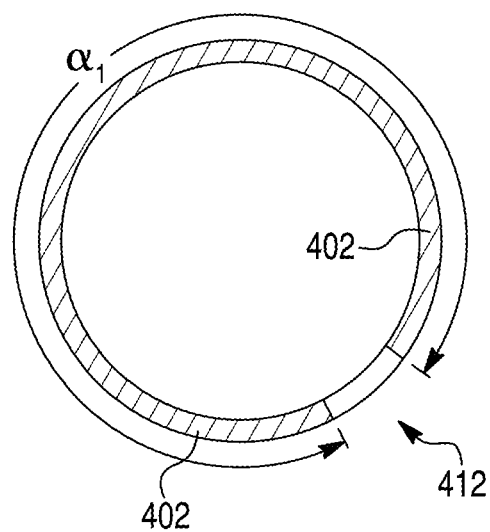
FIG. 7 shows a cross-sectional view taken along section line VII-VII in FIG. 5.

As seen in FIG. 7, length of a slot in the plurality of slots 412 may be defined by a slot angle $\alpha_1$, the slot angle being the center angle of the perpendicular plane $P_1$. The slot angle $\alpha_1$ may be any value between 0° and 350°, such as any integer between 0° and 350°. Also, the slot in one perpendicular plane $P_1$ may be about the same length or a different length from the slot in the adjacent perpendicular plane $P_1$.

As seen in FIG. 5, the slot in adjacent perpendicular planes can be separated by a predetermined separation distance $d_1$, which may be any suitable value such as any value between about 0.01 mm and about 0.1 mm, such as any 0.01 increment between 0.01 and 0.1 mm. The separation distance $d_2$ between the edge of slot in the perpendicular plane closest to the aperture 410 and the aperture 410 may be a value between about 0.01 mm and about 0.1 mm, such as any 0.01 increment between 0.01 and 0.1 mm. The separation distance $d_3$ between the edge of the slot in the perpendicular plane closest to the distal end 406 and the distal end 406 may be any value between about 0.05 mm and about 1.0 mm, such as any 0.01 increment between 0.05 and 1.0 mm, preferably about 0.25 mm.

The plurality of slots 414 shown in FIGS. 4 and 5 comprises two slots in different perpendicular planes $P_2$ in which the two slots run perpendicular to a longitudinal axis such that main extensions of the slot is in their respective plane $P_2$. Each slot in the plurality of slots 414 may a width $W_2$ and a length along its main extension. Preferably, the width $W_2$ of the slots 414 may be between about 0.01 to about 2.0 mm, preferably about 0.04 mm. The widths $W_2$ and $W_1$ may be the same or different from each other. As illustrated in FIG. 5, the slot in one perpendicular plane $P_2$ may be displaced in relation to the slot in an adjacent perpendicular plane $P_2$. Preferably, the slot in one perpendicular plane $P_2$ is displaced about 60° with respect to the slot in the adjacent perpendicular plane $P_2$. However, the degree of displacement may be any angle between 0° and 350°, such as any integer between 0° and 350°.

Figure 6:
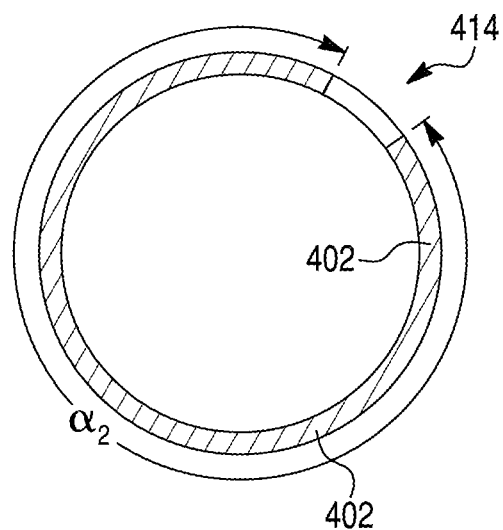
FIG. 6 shows a cross-sectional view taken along section line VI-VI in FIG. 5.

As seen in FIG. 6, the length of a slot in the plurality of slots 412 may be defined by a slot angle $\alpha_2$, the slot angle being the center angle of the perpendicular plane $P_2$. The slot angle $\alpha_2$ may be any value between 0° and 350°, such as any integer between 0° and 350°. The slot in one perpendicular plane $P_2$ may be about the same length or a different length from the slot in the adjacent perpendicular plane $P_2$.

As seen in FIG. 5, the adjacent perpendicular planes can be separated by a predetermined separation distance $d_4$, which may be any suitable value such as any value between about 0.01 mm and about 0.1 mm, such as any 0.01 increment between 0.01 and 0.1 mm. The separation distance $d_5$ between the edge of the plurality of slots in the perpendicular plane closest to the aperture 410 and the aperture 410 may be a value between about 0.01 mm and about 0.1 mm, such as any 0.01 increment between 0.01 and 0.1 mm. The separation distance $d_6$ between the edge of the plurality of slots in the perpendicular plane closest to the proximal end 408 and the proximal end 408 may be any value between about 0.05 mm and about 3.0 mm, such as any 0.01 increment between 0.05 and 3.0 mm, preferably about 1.0 mm.

According to other embodiments of the present invention, the plurality of slots 412 and 414 can be divided a plurality of sets of slots, wherein each set of slots is assigned to a perpendicular plane that runs perpendicular to a longitudinal axis such that main extensions of the slots within each set are in their respective plane. The lengths of the slots in a same perpendicular plane may be about equal. Also, the slots in the same perpendicular plane may be equally distributed around the circumference of the jacket. The slots in one perpendicular plane may be displaced in relation to the slots in an adjacent perpendicular plane.

For example, with regard to the plurality of slots 412, these slots may be divided into two, three, four or more sets of slots with each set on a different perpendicular plane $P_1$. Each set of slots may have one, two, three, four, or more slots in its respective perpendicular plane. Each slot in the plurality of slots 412 may a width $W_1$ that is about the same or different from width $W_2$ and a length along its main extension that is the same or different from the length(s) of the plurality of slots 414. The slots may be equally distributed around the circumferential surface.

With regard to the plurality of slots 414, these slots may be divided into two, three, four or more sets of slots with each set on a different perpendicular plane $P_2$. Each set of slots may have two, three, four, or more slots in its respective perpendicular plane. Each slot in the plurality of slots 414 may a width $W_2$ and a length along its main extension. The slots may be equally distributed around the circumferential surface.

The slots in one perpendicular planes $P_1$, $P_2$ may be displaced in relation to the slots in an adjacent perpendicular plane $P_1$, $P_2$. Preferably, the slots in one perpendicular plane $P_1$, $P_2$ are displaced approximately 10° with respect to each adjacent perpendicular plane $P_1$, $P_2$. However, the degree of displacement may be any angle between 0° and 350°, such as any integer between 0° and 350°.

The slots in each set of the plurality of slots 412, 414 may be about the same length or a different length. Also, the lengths of the slots may change from set to set. For example, the length of a slot in the plurality of slots 412 may be defined by a slot angle, the slot angle being the center angle of the perpendicular plane $P_1$. The slot angle may be any value between 0° and 170°, such as any integer between 0° and 170°.

The number of perpendicular planes $P_1$ and $P_2$ may also be varied. For example, the number of perpendicular planes $P_1$ may be one, two, three, four, five, or more and the number of perpendicular planes $P_2$ may be one, two, three, four, five or more. For any number of perpendicular planes, the number of slots per plane may be any suitable number, such as one, two, three, four, or more. Further, the number of slots per plane may vary between adjacent planes.

The jacket 205, 305 may a constant cross section (such as a constant thickness) along its entire length with the exception of the aperture 410 and the plurality of slots 412, 414. The outer diameter of the jacket 205, 305 acts as a portion of the outer surface of the sensor guide wire assembly. The jacket 205, 305 may be made from any suitable material such as stainless steel or a super elastic alloy, such as Nitinol, copper-tin, copper-zinc, or copper-zinc-tin.

As a matter of assembly, the core wire(s), the coil, and/or the arced tip may be connected by, for example, laser welding, adhesives, soldering, or other suitable mechanism. The coil, the core wire(s), the proximal tube portion, or any combination thereof are joined to the jacket by, for example, laser welding, adhesives, soldering, or other suitable mechanism.

The use of the slots in the jacket 205, 305 permits the jacket to be more bendable and thus makes the sensor guide wire assembly more maneuverable for the health care professional when snaking the sensor guide wire assembly through the blood vessel network of the patient's body. Essentially, because the jacket is more bendable, the rigid sensor portion of the sensor guide wire assembly becomes shorter. Thus, snaking the sensor guide wire assembly through the tortuous paths of the blood vessel network become easier.

Figure 8:
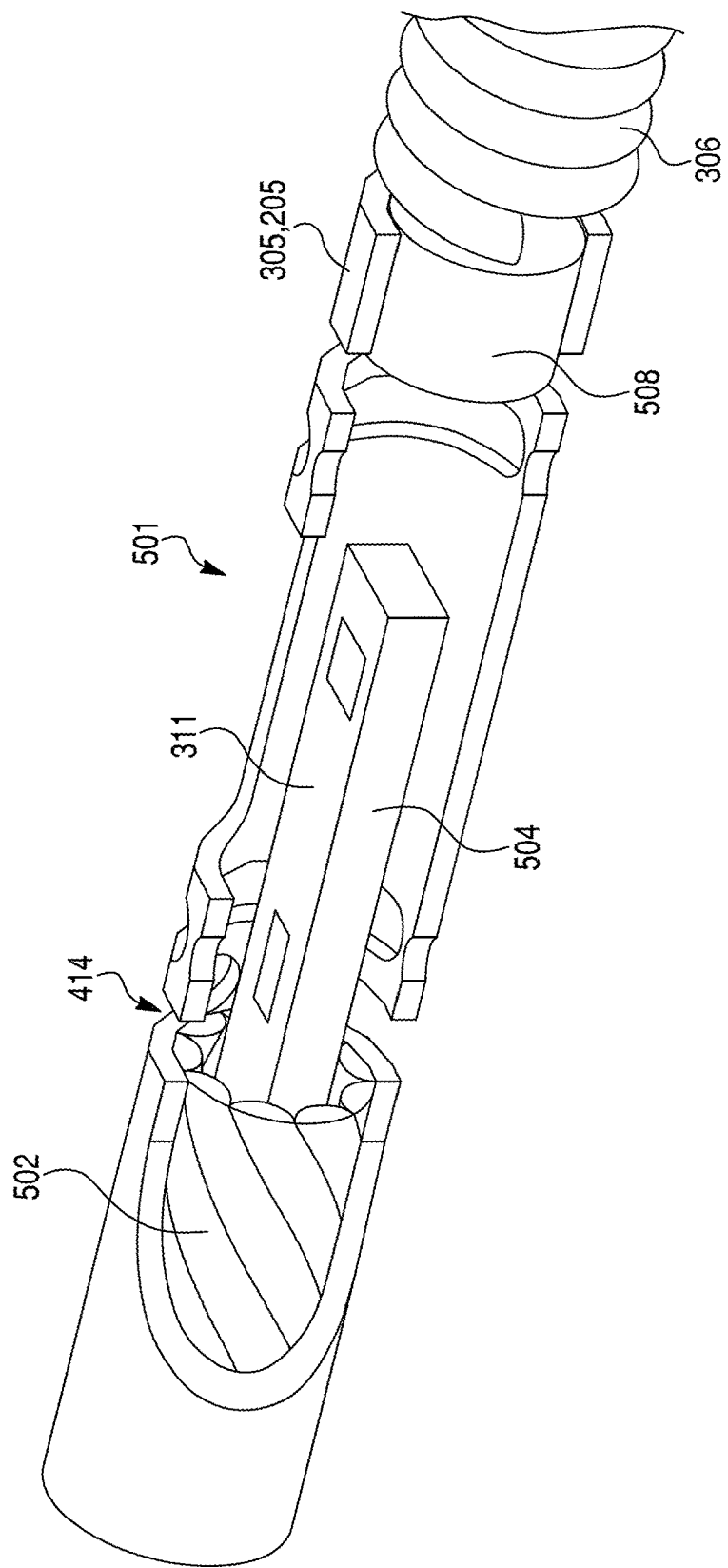
FIG. 8 shows a cut away view of a sensor guide wire used in the system of FIG. 1 according to another embodiment of the present invention.

FIG. 8 shows a cut away view of a sensor guide wire 501 used in the system of FIG. 1 according to another embodiment of the present invention. The sensor guide wire 501 is the same as the sensor guide wire shown in FIGS. 3-4, but has a mounting structure 502 for mounting the sensor element 311 and a core wire 508, instead of the core wire 308.

The mounting structure 502 is placed within either a portion of the jacket or sleeve 305, with a portion of the proximal tube portion 303, or a combination thereof. For example, the mounting structure may extend into the jacket 305 up to the proximal-most slot 414 and/or extend into the proximal tube portion up to and including about 500 mm, such as, for example, 280 mm.

The mounting structure 502 may be stranded wire forming a hollow tube, and made of any suitable material, such as stainless steel, for example 305 stainless steel. The mounting structure 502 may be held in the jacket and/or proximal tube portion by friction, epoxy, welding, soldering, or any other suitable mechanism. The mounting structure 502 may be encapsulated by glue, epoxy, a silicone based material, or any other suitable material. For example, the outer dimensions of the mounting structure may match the inner dimensions of the jacket and/or proximal tube portion so as to have a friction fit or a slip fit or a press fit.

The mounting structure then holds the circuit board 504 of the sensor element 311. The sensor element may be any suitable material. The circuit board 504 may be fixed to the mounting structure 502 by friction, epoxy, welding, soldering or any other suitable mechanism. For example, the outer dimensions of the circuit board may match the inner dimensions of the mounting structure so as to have a friction fit or a slip fit or a press fit.

The core wire 508 is similar to the core wire 208 of FIG. 2 in that it extends in the distal end portion of the sensor guide wire assembly. Indeed, the mounting structure 502 may be used in the embodiment of FIG. 2. The proximal end of the core wire 508 can be an enlarged portion which is secured in the distal portion of the jacket 30 by friction, epoxy, welding, soldering or any other suitable mechanism. The coil 306 may be attached to the jacket 305, 205 or the enlarged portion of the core wire 508 in the same manner as the coil in FIG. 3.

The mounting structure 502 being used to mount the sensor element 311 may permit the sensor element 311 to be freely suspended such that a core wire is not necessary in the jacket or sleeve 205, 305. Thus, more space is added inside the jacket 205, 305 and provide easier assembly because there are less joints to connect. The mounting structure 502 may also be a ground tube with or without slots cut therein or a tube made from Nitinol.

Figure 9:
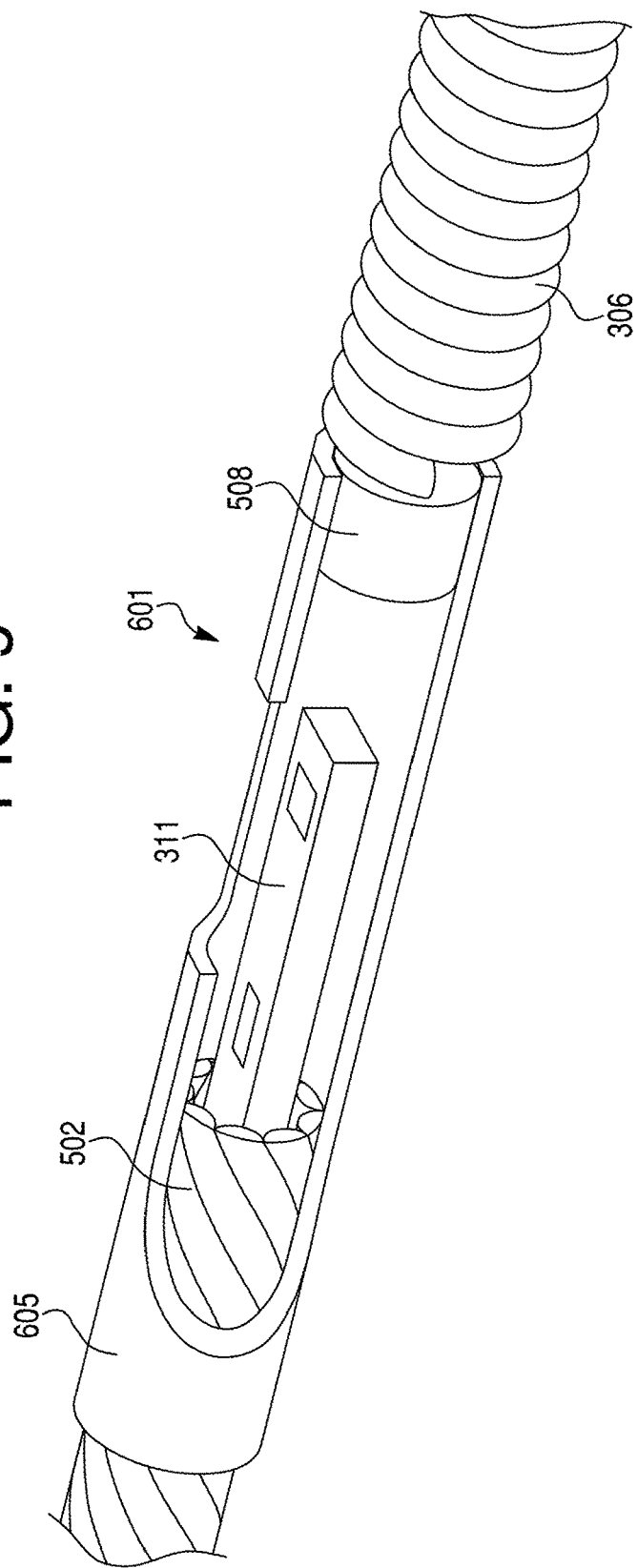
FIG. 9 shows a cut away view of a sensor guide wire used the system of FIG. 1 according to another embodiment of the present invention.
Figure 10A:
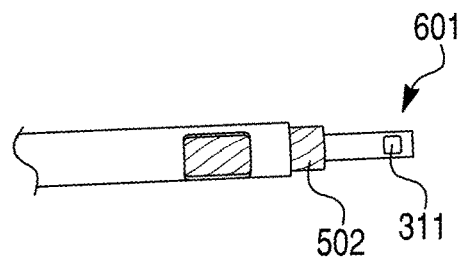
FIGS. 10A-10C show various plan view of the sensor guide wire of FIG. 9.
Figure 10B:
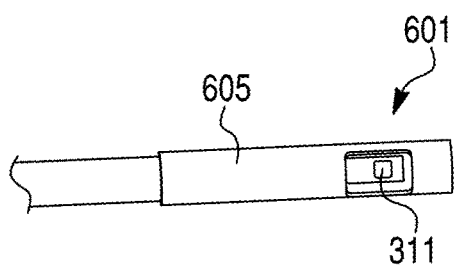
Figure 10C:
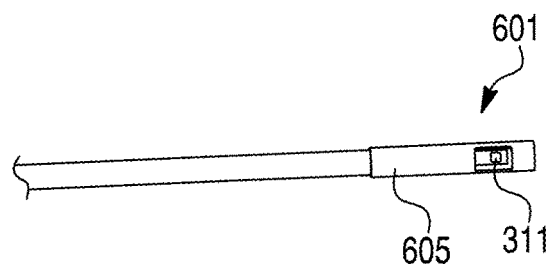

FIG. 9 shows a cut away view of a sensor guide wire 601 used in the system of FIG. 1 according to another embodiment of the present invention. The sensor guide wire 601 is the same as the sensor guide wire shown in FIG. 8, but has a different jacket 605.

The jacket 605 is the same as the jacket 205, 305 in FIGS. 2-8, but does not include the slots 412 and 414. Furthermore, the jacket 605 may be used as the jacket in the embodiment of FIG. 2 having the mounting structure 502.

The sensor guide wire of any of the above embodiments may be used to measure any variety of physiological variables, such as blood pressure, blood temperature, blood flow, FFR, or the concentration or presence of one of more blood analytes.

The sensor guide wire of any of the above embodiments may also be used as a guide for a catheter which is pushed over the outer surface of the guide wire.

Besides those embodiments depicted in the figures and described in the above description, other embodiments of the present invention are also contemplated. For example, any single feature of one embodiment of the present invention may be used in any other embodiment of the present invention. For example, the following is a list of embodiments, but the invention should not be viewed as being limited to these embodiments.

(I) A sensor guide wire for an intravascular measurement of a physiological variable in a living body, comprising: a proximal tube portion; a distal end portion; and a sensor element configured to measure the physiological variable based on exposure to fluid in the living body.

(II) The sensor guide wire according to any of the Roman-numbered embodiments above or below, further comprising a cylindrical-shaped jacket forming an interior space housing the sensor element and extending from a distal end of the proximal tube portion to a proximal end of the distal end portion.

(III) The sensor guide wire according to any of the Roman-numbered embodiments above or below, wherein the jacket comprises an outer circumferential wall with a circumferential surface extending between distal and proximal longitudinal ends of the jacket, wherein the outer circumferential wall includes at least one aperture along its circumferential surface so as to permit passage of the fluid through the outer circumferential wall.

(IV) The sensor guide wire according to any of the Roman-numbered embodiments above or below, wherein the outer circumferential wall further includes a plurality of slots located between the at least one aperture of the outer circumferential wall and one of the distal and proximal ends of the jacket.

(V) The sensor guide wire according to any of the Roman-numbered embodiments above or below, wherein the jacket has a length of about 0.5 mm to 10 mm.

(VI) The sensor guide wire according to any of the Roman-numbered embodiments above or below, wherein the plurality of slots is located between the at least one aperture of the outer circumferential wall and the proximal end of the jacket.

(VII) The sensor guide wire according to any of the Roman-numbered embodiments above or below, wherein the outer circumferential wall further includes another plurality of slots located between the at least one aperture of the outer circumferential wall and the distal end of the jacket.

(VIII) The sensor guide wire according to any of the Roman-numbered embodiments above or below, wherein the plurality of slots are divided into a plurality of sets of slots, and wherein each set of slots is assigned to a perpendicular plane that runs perpendicular to a longitudinal axis such that main extensions of the slots within each set are in their respective plane.

(IX) The sensor guide wire according to any of the Roman-numbered embodiments above or below, wherein the lengths of the slots in a same perpendicular plane are essentially equal.

(X) The sensor guide wire according to any of the Roman-numbered embodiments above or below, wherein the slots in a same perpendicular plane are equally distributed around the circumference of the jacket.

(XI) The sensor guide wire according to any of the Roman-numbered embodiments above or below, wherein slots in one perpendicular plane are rotationally displaced in relation to slots in an adjacent perpendicular plane.

(XII) The sensor guide wire according to any of the Roman-numbered embodiments above or below, further comprising a mounting structure supporting the sensor element in a freely suspended manner in a lumen within the sensor guide wire.

(XIII) The sensor guide wire according to any of the Roman-numbered embodiments above or below, wherein the mounting structure is a stranded hollow wire fixed within the proximal tube portion.

(XIV) The sensor guide wire according to any of the Roman-numbered embodiments above or below, further comprising a cylindrical-shaped jacket forming an interior space housing the sensor element and extending from a distal end of the proximal tube portion to a proximal end of the distal end portion.

(XV) The sensor guide wire according to any of the Roman-numbered embodiments above or below, wherein the mounting structure is a stranded hollow wire fixed within the jacket.

The present invention is not limited to the above-described preferred embodiments. Various alternatives, modifications and equivalents may be used. Therefore, the above embodiments should not be taken as limiting the scope of the invention.

What is claimed is:

1. A sensor guide wire for an intravascular measurement of a physiological variable in a living body, comprising:
    a proximal tube portion;
    a distal end portion;
    a sensor element configured to measure the physiological variable based on exposure to fluid in the living body; and
    a cylindrical-shaped jacket forming an interior space housing the sensor element and extending from a distal end of the proximal tube portion to a proximal end of the distal end portion, wherein a length of the jacket is in a range of 1 mm to 3 mm,
    wherein the jacket comprises an outer circumferential wall with a circumferential surface extending between distal and proximal longitudinal ends of the jacket,
    wherein the outer circumferential wall includes at least one aperture along its circumferential surface so as to permit passage of the fluid through the outer circumferential wall,
    wherein the outer circumferential wall further includes a plurality of slots located between the at least one aperture of the outer circumferential wall and one of the distal or proximal longitudinal ends of the jacket, and
    wherein the slots are elongated in a circumferential direction around the outer circumferential wall of the jacket.

2. The sensor guide wire according to claim 1, wherein the plurality of slots is located between the at least one aperture of the outer circumferential wall and the proximal longitudinal end of the jacket.

3. The sensor guide wire according to claim 2, wherein the outer circumferential wall further includes another plurality of slots located between the at least one aperture of the outer circumferential wall and the distal longitudinal end of the jacket.

4. The sensor guide wire according to claim 1, wherein the plurality of slots are divided into a plurality of sets of slots, and wherein each set of slots is assigned to a perpendicular plane that runs perpendicular to a longitudinal axis such that main extensions of the slots within each set are in their respective plane.

5. The sensor guide wire according to claim 4, wherein lengths of the slots in a same perpendicular plane are essentially equal.

6. The sensor guide wire according to claim 4, wherein the slots in a same perpendicular plane are equally distributed around the circumference of the jacket.

7. The sensor guide wire according to claim 4, wherein slots in one perpendicular plane are rotationally displaced in relation to slots in an adjacent perpendicular plane.

8. The sensor guide wire according to claim 1, wherein collectively, the plurality of slots extend entirely around the outer circumferential wall of the jacket in the circumferential direction.

* * * * *